United States Patent
Govro et al.

(10) Patent No.: US 9,940,578 B1
(45) Date of Patent: Apr. 10, 2018

(54) SYSTEMS AND METHODS FOR DISRUPTING UNDESIRABLE OUTCOMES

(71) Applicant: Sphere3, LLC, Kansas City, KS (US)

(72) Inventors: Kourtney Govro, Peculiar, MO (US); Kristal Rayson, Independence, MO (US); Steven Kent Mills, Overland Park, KS (US); Kyle Evans, Faucett, MO (US); David Govro, Peculiar, MO (US); Devon Kerns, Savannah, MO (US)

(73) Assignee: Sphere3, LLC, Kansas City, MO (US)

( * ) Notice: Subject to any disclaimer, the term of this patent is extended or adjusted under 35 U.S.C. 154(b) by 429 days.

(21) Appl. No.: 14/328,533

(22) Filed: Jul. 10, 2014

Related U.S. Application Data

(60) Provisional application No. 61/844,718, filed on Jul. 10, 2013.

(51) Int. Cl.
*G06N 5/02* (2006.01)

(52) U.S. Cl.
CPC ..................................... *G06N 5/02* (2013.01)

(58) Field of Classification Search
None
See application file for complete search history.

(56) References Cited

U.S. PATENT DOCUMENTS

| | | | |
|---|---|---|---|
| 6,151,581 A | 11/2000 | Kraftson et al. | |
| 7,769,626 B2 | 8/2010 | Reynolds | |
| 8,512,240 B1 * | 8/2013 | Zuckerman-Stark | A61B 5/02 128/924 |
| 8,972,272 B1 | 3/2015 | Dvorak et al. | |
| 2002/0010596 A1 | 1/2002 | Matory | |
| 2004/0122294 A1 * | 6/2004 | Hatlestad | A61B 5/0031 600/300 |
| 2004/0122297 A1 * | 6/2004 | Stahmann | A61B 5/02055 600/300 |
| 2004/0122704 A1 | 6/2004 | Sabol et al. | |

(Continued)

OTHER PUBLICATIONS

File History of U.S. Appl. No. 13/795,501, filed Mar. 12, 2013, and entitled Systems and Modules for mproving Patient Satisfaction; Applicant: Sphere3, LLC.

(Continued)

*Primary Examiner* — Alan S Chen
(74) *Attorney, Agent, or Firm* — Erise IP, P.A.

(57) ABSTRACT

Systems and methods set forth herein may aid in identifying and disrupting undesirable outcomes. The system may include computer readable media; an electronic input device; an output device; a processor in data communication with the input device and the output device; and electronic instructions. The electronic instructions, when executed by the at least one processor, perform steps for: automatically storing event data from the electronic input device in the computer readable media; actuating the output device to graphically display the event data; determining if the event data qualifies as a critical event; storing the critical event data as outcome data in the computer readable media; accessing the event data and outcome data; determining at least one correlation between the event data and the outcome data; actuating the output device to display an intervention to aid in disrupting future critical events; and storing the intervention in the computer readable media.

18 Claims, 2 Drawing Sheets

(56) References Cited

U.S. PATENT DOCUMENTS

| | | | |
|---|---|---|---|
| 2005/0010165 A1* | 1/2005 | Hickle | A61B 5/417 604/66 |
| 2006/0181424 A1 | 8/2006 | Graves et al. | |
| 2007/0150024 A1* | 6/2007 | Leyde | A61B 5/0476 607/45 |
| 2008/0059230 A1 | 3/2008 | Manning et al. | |
| 2008/0133290 A1 | 6/2008 | Siegrist et al. | |
| 2009/0198509 A1 | 8/2009 | Dumoff | |
| 2010/0241455 A1 | 9/2010 | Gilbert et al. | |
| 2011/0112852 A1 | 5/2011 | Ware et al. | |
| 2011/0153349 A1 | 6/2011 | Anderson et al. | |
| 2011/0225006 A1 | 9/2011 | Manning et al. | |
| 2012/0078661 A1 | 3/2012 | Sheldon et al. | |
| 2012/0323090 A1 | 12/2012 | Bechtel et al. | |
| 2012/0330677 A1 | 12/2012 | Velimesis | |
| 2013/0245389 A1* | 9/2013 | Schultz | A61B 5/0002 600/301 |
| 2013/0325508 A1* | 12/2013 | Johnson | G06F 19/3418 705/3 |
| 2014/0019468 A1* | 1/2014 | Federoff | G06F 19/322 707/758 |

OTHER PUBLICATIONS

File History of U.S. Appl. No. 14/203,280, filed Mar. 10, 2014, and entitled Systems and Modules for Improving Patient Satisfaction; Applicant: Sphere3, LLC.

* cited by examiner

SYSTEMS AND METHODS FOR DISRUPTING UNDESIRABLE OUTCOMES

RELATED APPLICATIONS

This application claims priority to provisional patent application No. 61/844,718 filed Jul. 10, 2013, the disclosure of which is incorporated in its entirety by reference herein.

BACKGROUND

Undesirable outcomes can often be prevented by recognizing a series of events leading to the outcome and taking affirmative steps to avoid the undesirable outcome. Especially in the healthcare industry, it is desirable to avoid events that contribute to or cause outcomes harmful to the health of a patient. Systems, modules, and methods set forth herein may aid in identifying and disrupting undesirable outcomes.

SUMMARY

The following presents a simplified summary of the invention in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented below.

In one embodiment, a system for identifying and disrupting undesirable outcomes includes computer readable media; an electronic input device; an output device; a processor in data communication with the input device and the output device; and electronic instructions. The electronic instructions, when executed by the at least one processor, perform steps for: (a) automatically storing event data from the electronic input device in the computer readable media; (b) actuating the output device to graphically display the event data; (c) determining if the event data qualifies as a critical event; (d) storing the critical event data as outcome data in the computer readable media; (e) accessing the event data and outcome data; (f) determining at least one correlation between the event data and the outcome data; (g) actuating the output device to display an intervention to aid in disrupting future critical events; and (h) storing the intervention in the computer readable media.

In another embodiment, a system for identifying and disrupting undesirable outcomes includes computer readable media; an electronic input device; an output device; a processor in data communication with the input device and the output device; and electronic instructions. The electronic instructions, when executed by the at least one processor, perform steps for: (a) automatically storing event data from the electronic input device in the computer readable media; (b) actuating the output device to graphically display the event data; (c) determining if the event data qualifies as a critical event; (d) storing the critical event data as outcome data in the computer readable media; (e) accessing the event data and outcome data; (f) determining at least one correlation between the event data and the outcome data; (g) actuating the output device to display a first intervention to aid in disrupting future critical events based on the correlation between the event data and the outcome data; (h) storing the first intervention in the computer readable media; (i) repeating steps (a) and (b)-(d); (j) accessing the outcome data and the first intervention; (j) determining at least one correlation between the outcome data and the first intervention; and (k) actuating the output device to display a second intervention to aid in disrupting future critical events based on the correlation between the outcome data and the first intervention.

In still another embodiment, a system for identifying and disrupting undesirable outcomes in an acute healthcare environment has computer readable media; an electronic medical input device; a voluntary input device; an output device; a processor in data communication with the input devices and the output device; and electronic instructions. The electronic instructions, when executed by the at least one processor, perform steps for: (a) automatically storing event data from the electronic input device in the computer readable media; (b) storing action data from the voluntary input device in the computer readable media; (c) accessing the event data and the action data; (d) actuating the output device to graphically display the action data and the event data; (e) determining if the action data and the event data qualify as a critical event; (f) storing the critical event as outcome data in the computer readable media; (g) accessing the event data, action data, and outcome data; (h) determining at least one correlation between the action data, the event data, and the outcome data; (i) determining a first intervention to aid in disrupting future critical events based on the correlation between the action data, the event data, and the outcome data; (j) actuating the output device to display the first intervention; (k) storing the first intervention in the computer readable media; (l) accessing the first intervention and the outcome data; (m) determining at least one correlation between the outcome data and the first intervention; (n) determining a second intervention to aid in disrupting future critical events based on the correlation between the outcome data and the first intervention; and (o) actuating the output device to display the second intervention.

According to still yet another embodiment, a method for identifying and disrupting undesirable outcomes in a healthcare environment is disclosed. The method includes providing computer readable media; providing at least one electronic medical input device, the medical input device being outwardly associated with a patient; providing a voluntary input device; providing an output device; providing a processor; and utilizing the processor to execute a series of steps. The execution of the steps occurs in accordance with instructions stored on the computer readable media and accessed by the processor. The steps include: (a) automatically storing event data from the medical input device; (b) storing action data from the voluntary input device; (c) accessing the event data and the action data; (d) actuating the output device to graphically display the action data and the event data; (e) determining if the action data and the event data qualify as a critical event; (f) storing the critical event as outcome data; (g) accessing the event data, the action data, and the outcome data; (h) determining at least one correlation between the action data, the event data, and the outcome data; (i) actuating the output device to display a first intervention to aid in disrupting future critical events based on the correlation between the action data, the event data, and the outcome data; (j) storing the first intervention; (k) repeating steps (a)-(c), (e), and (f); (l) accessing the outcome data and the first intervention; (m) determining at least one correlation between the outcome data and the first intervention; and (n) actuating the output device to display a second intervention to aid in disrupting future critical events based on the correlation between the outcome data and the first intervention. The event data is medical data associated with the patient; and the critical event is determined based on predetermined criteria that recognize events adverse to the health of the patient.

BRIEF DESCRIPTION OF THE DRAWINGS

Illustrative embodiments of the present invention are described in detail below with reference to the attached figures.

WRITTEN DESCRIPTION

Figure 1:
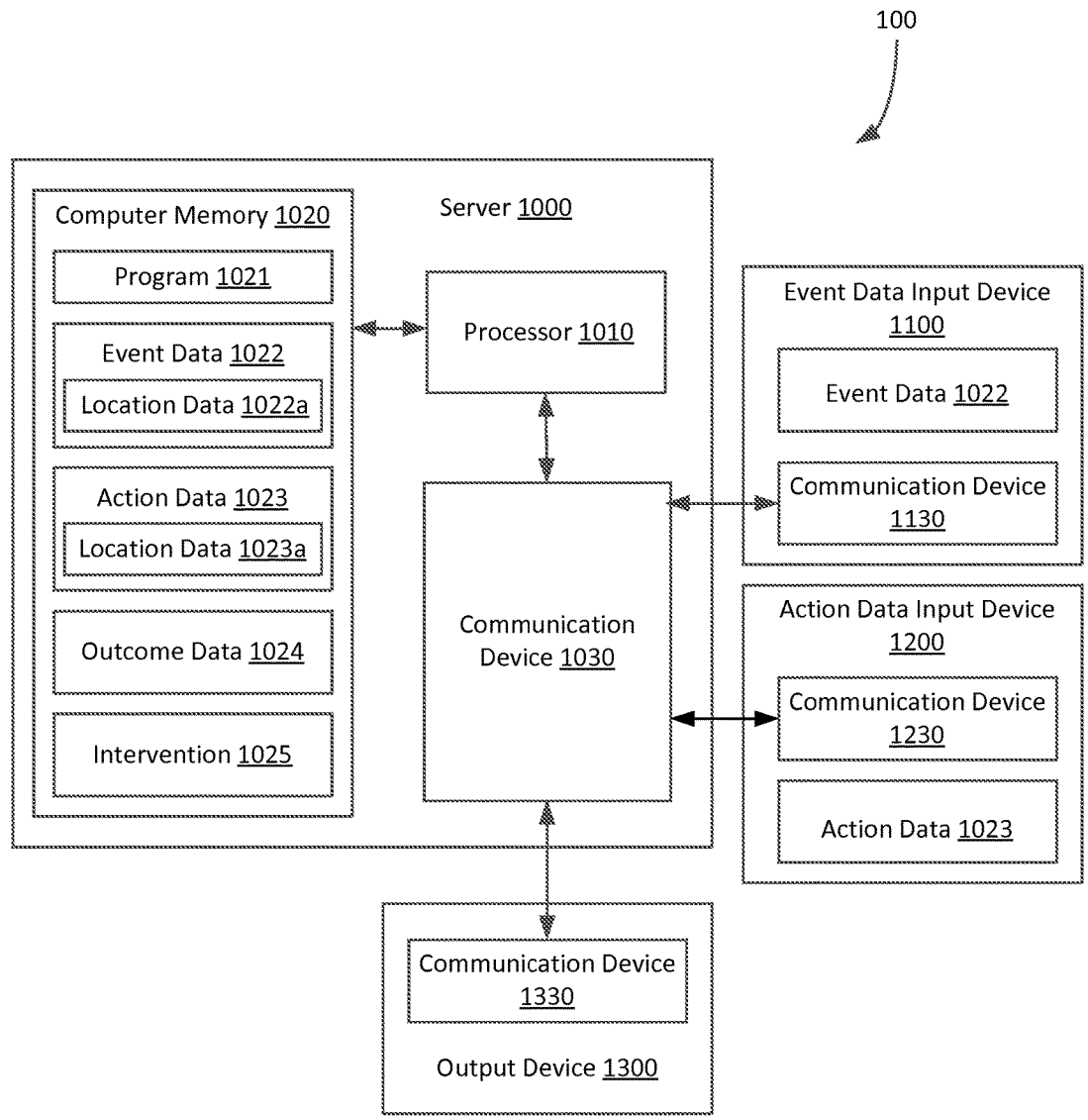
FIG. 1 is a detailed view of a system according to one embodiment of the current invention, in use at a single location.

Embodiments of the present invention disclose systems and methods to aid in the identification and disruption of undesirable outcomes. FIG. 1 illustrates a system 100 for identifying and preventing potentially adverse outcomes according to one embodiment of the current invention. Generally, the system 100 includes a server 1000, at least one event data input devices 1100, at least one action data input device 1200, and at least one output device 1300.

The event data input device 1100 may include, for example, medical devices associated with a patient but external to the patient's body. For example, the event data input devices 1100 may include IV pumps, vents, telemetry monitors, nurse call lights, electronic medical records (EMR), location monitors, thermometers, et cetera. Multiple event data input devices 1100 may provide event data 1022 for a particular patient at one time.

Those skilled in the art will appreciate that the various elements discussed herein may be separated into multiple elements or portions (housed at either the same place, or at different places), or may be combined into fewer elements and portions. For example, the server 1000 may, in use, be either one server or multiple servers in communication with one another. Further, the output device 1300 and the action data input device 1200 may be separate devices (e.g., the output device 1300 may be a printer, a monitor, et cetera while the action data input device 1200 may be a keyboard, a mouse, a touch pad, et cetera) or combined into a single device (e.g., a touchscreen). The configuration of the action data input device 1200 and the output device 1300 is insignificant unless otherwise noted herein, or as would be apparent to one of ordinary skill in the art.

The system 100 may be in use at multiple locations. Specifically, additional event data input devices 1100 and action data input devices 1200 may be provided. The term "location" herein is used broadly, and may be, for example, a patient room, a particular hall (or floor or unit within a medical facility), an entire medical facility, medical facilities within a geographic area, or similar medical units (e.g., cardiology, oncology, etc.) within a geographic area. The term "location level" is used to refer to locations within a single medical facility, while term "multi-location level" is used to refer to locations that are not housed within a single medical facility (e.g., medical facilities within a geographic area, or similar medical units within a geographic area). A time component and/or unique patient identifiers may additionally be utilized within the terms "location", "location level", and "multi-location level" such that, for example, data associated with patient room(s) at a particular time (and thus particular patients) may be analyzed.

Continuing with FIG. 1, the server 1000 has a processor 1010 in data communication with computer memory 1020 and a communication device 1030 for use in interfacing with the event data input device 1100, the output device 1300, and the action data input device 1200. As described above, the processor 1010, computer memory 1020, and the communication device 1030 may in some embodiments be optionally separated into multiple elements and dispersed.

The computer memory 1020 may include volatile and non-volatile memory, and any appropriate data storage devices whether now existing or later developed may be utilized. The computer memory 1020 may store a program 1021, event data 1022, action data 1023 (e.g., data regarding actions taken with a patient, such as medicament administration), outcome data 1024 (e.g., action data or event data determined to be a critical event), and interventions 1025, each of which is discussed in greater detail below. Additionally, location data 1022a may be associated with the event data 1022 (e.g., where the event data 1022 came from, and what location should be associated with the event data 1022); location data 1023a may also be associated with the action data 1023 to keep a record of where the action occurred.

The communication device 1030 may be any device, whether now known or later developed, that allows the processor 1010 to communicate with the event data input device 1100, the output devices 1300, and the action data input devices 1200. For example, the communication device 1030 may be a modem and/or a port for providing wired access to the processor 1010.

The event data input device 1100 may be any device that obtains event data 1022 and interacts automatically with the server 1000 to store the event data 1022 in the computer memory 1020. The event data 1022 may be automatically pushed to the server 1000, or the server 1000 may automatically pull the event data 1022 from the event data input device 1100. As described above, the event data input device 1100 may be, for example, any device external to a patient that provides information relating to the patient, the patient's care, or the patient's location. The event data 1022, therefore, is data relating to the patient, the patient's care, or the patient's location as provided by the event data input device 1100, and may include data regarding a patient's vital signs, activation of a nurse call light, operation of a ventilator device, operation of an IV pump, information about the patient as retrieved from the EMR, the patient's medical condition, temperature of the patient's location (e.g., temperature in a patient's room), physiological data (e.g., O2 saturation levels, blood pressure, etc.), interactive beds, et cetera.

The action data input device 1200 may be any device that obtains action data 1023 and allows the action data 1023 to be stored in the computer memory 1020. Action data 1023 may include data relating to patient activity that is not (or cannot be) automatically input to the system via the event data input device 1100. For example, a nurse might administer an oral medication to a patient and record, via the event data input device 1100, the medication and dose, and the time of administration. The action data 1023 may be stored directly in the computer memory 1020 from the action data input device 1200, or may be added to the computer memory 1020 via the server 1000.

The action data input device 1200 and the output device 1300 may be any appropriate devices, whether now existing or later developed, for providing data to and presenting data from the processor 1010. This may include, for example, a printer, a monitor, a keyboard, a computer mouse, a touch pad, and a touchscreen. The input devices 1100, 1200 and output device 1300 are shown to each have communication devices 1130, 1230, and 1330 for communicating with the communication device 1030.

Figure 2:
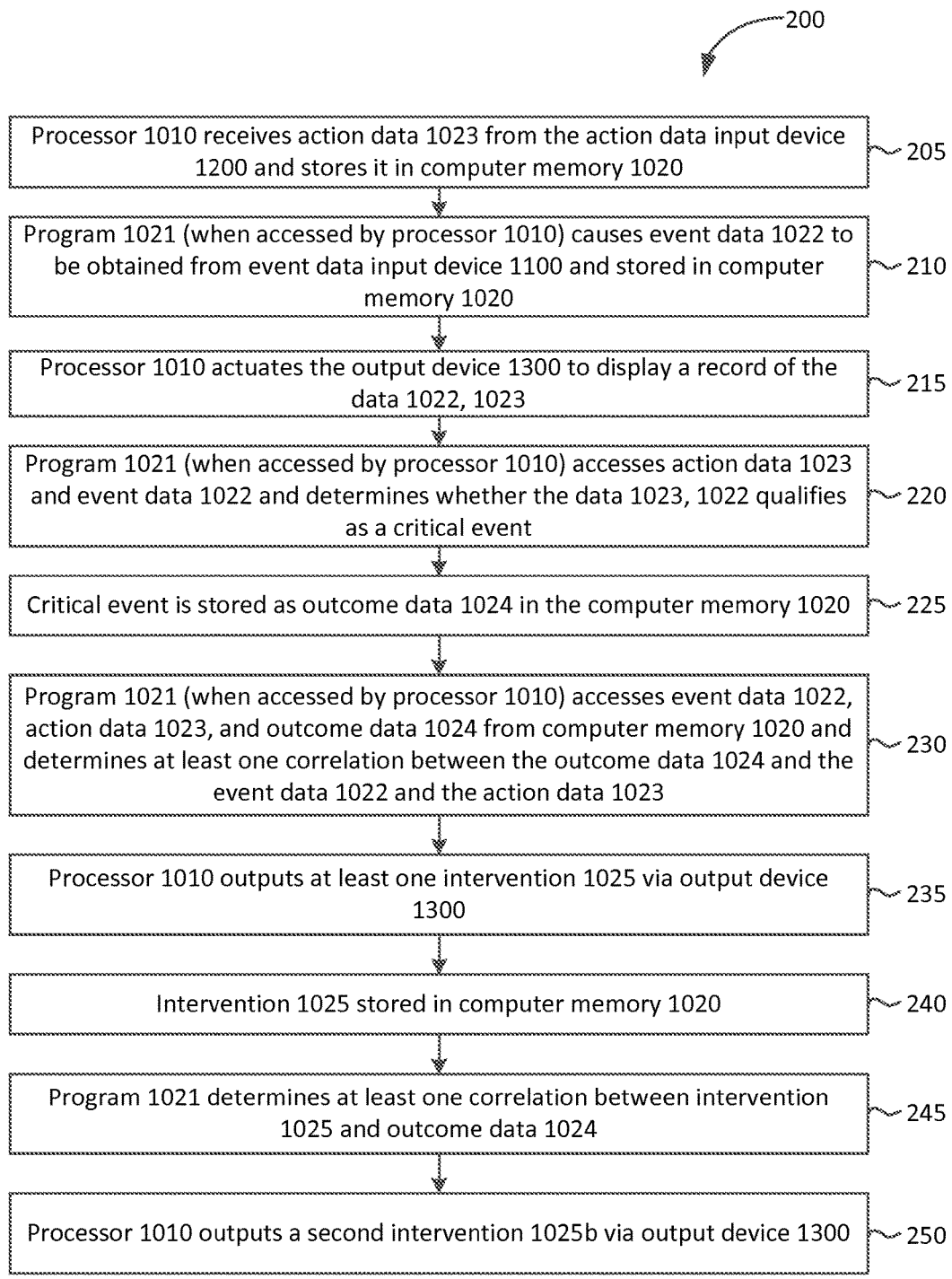
FIG. 2 is an exemplary set of steps performed by the system of FIG. 1.

The program 1021 includes instructions for operating the system 100. In some embodiments, the program 1021 may be dispersed or duplicated (e.g., in the input devices 1100, 1200). The following description, which references FIG. 2, is an example of a process 200 performed by the system 100 operating in accordance with the program 1021. Those skilled in the art will recognize that the various steps described may be performed in alternate orders, combined together, or broken into additional steps.

At step 205, the processor 1010 receives action data 1023 from the action data input device 1200 and stores the action data 1023 in the computer memory 1020. At step 210, the program 1021, when accessed by the processor 1010, causes the event data 1022 to be obtained from the event data input device 1100 and stored in the computer memory 1020 (e.g., in a database).

Having retrieved the action data 1023 and the event data 1022, the process moves to step 215, where the processor 1010 actuates the output device 1300 to display a record of the data 1022, 1023. The record may be, for example, a graphical representation of the data such as a scatter plot for easy recognition. The system thus provides data visualization that allows users to easily identify and analyze metrics associated with patient care, including when certain events occurred, when a particular patient indicated a need via a medical device such as a nurse call light and how long the patient waited to have the need met, how often assistance was requested and whether assistance was provided, where patients and caregivers were located, et cetera.

The process then moves to step 220, where the program 1021 accesses the action data 1023 and the event data 1022 in the computer memory 1020 and determines if the data qualifies as a critical event. If a critical event is determined to have occurred, the data is converted to outcome data 1024, and is stored in the computer memory 1020 at step 225. A critical event may be predetermined events that are considered adverse to a patient's health. Examples of critical events include a patient fall, incorrect medication administration, severe increase or decrease in blood pressure, et cetera.

Moving on, at step 230, the program 1021 accesses the action data 1023, the event data 1022, and the outcome data 1024 from the computer memory 1020 and determines at least one correlation between the outcome data 1024, the action data 1023, and the event data 1022. In some situations, the correlations may be dependent upon a single variable, while in other situations multiple variables may be of interest. For example, ingestion of a particular medication may be correlated to an increased number of patient falls. Or, ingestion of a particular medication within a certain time of doing something else (e.g., ingesting another particular medication) may be correlated to an increased number of patient falls or a rapid increase of blood pressure.

The process then moves to step 235, where the program 1021 causes the processor 1010 to output a first intervention 1025*a* via the output device 1300 to aid in disrupting the potentially undesirable outcomes based on the correlation between the event data 1022, the action data 1023, and the outcome data 1024. Using the example provided above, if the program 1021 determines that a correlation exists between patients ingesting two medications within a certain period of time and patient falls, the output device 1300 may output instructions to take particular care to avoid situations in which patients can fall, or may output instructions to alter one of the medications.

These interventions 1025 may be stored in the computer memory, as indicated at step 240. Storing the interventions 1025 in the computer memory 1020 may allow the processor 1010 (utilizing the pattern recognition instructions of the program 1021) to further determine correlations between the intervention 1025 and outcome data 1024, as shown at step 245, and make adjustments based on the results should the intervention 1025 fail to result in decreased adverse outcomes. In staying with the above example, a first intervention 1025*a* in situations where two medications are ingested within a period of time may be instructions to take particular care with the patient. If the adverse outcome (i.e., reduced patient falls) is not eliminated or reduced, the processor 1010 may access the event data 1022, the action data 1023, the outcome data 1024, and the first intervention 1025*a* and determine a second correlation. The processor 1010 may then cause the output device 1300 to output a second intervention 1025*b*, as shown at step 250, based on the correlation between the data 1022, 1023, 1024 and the first intervention 1025*a*. In our example, the second intervention 1025*b* may be to suggest altering the timing of administering the medications to the patient. In this way, the effectiveness of the interventions may be compared to one another and/or combined together, allowing the processor 1010 to determine the most effective intervention 1025 for future situations.

Multiple solutions may exist for a particular problem. In some embodiments, the processor 1010 may interact with a pricing or cost module to determine which solution is, for example, lower cost, and the output device 1300 may output an intervention 1025 consistent with the processor's determination. In other embodiments, the processor 1010 may determine that certain interventions are superior in some situations. For example, suggesting altering the timing of medication delivery may be superior in some situations where making such a change is relatively likely to occur (e.g., during times when a doctor is readily available to consent to such a change) yet less effective in other situations (e.g., when the doctor is less available).

Particularly when the system is used at multiple facilities, correlations between the event data 1022, the action data 1023, and the outcome data 1024, as well as correlations between the interventions 1025 and outcome data 1024 may be determined at both a location level and a multi-location level in steps 230 and 245. At steps 235 and 250, then, interventions 1025 may be made at both the location level and the multi-location level.

Practitioners in the field of acute healthcare may immediately recognize the value of the systems and methods set forth herein, and the systems and methods have been described with that in mind. However, the systems and methods described are not limited to the acute healthcare setting, and may be valuable in many other settings and industries, including long-term care settings, retirement community settings, behavioral health settings, et cetera.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Various steps in described methods may be undertaken simultaneously or in other orders than specifically provided. While various software have been described as enabling specific functions, those skilled in the art will appreciate that the files and software may be commingled or further segregated, and that specific file or software labels are used for convenience.

What is claimed is:

1. A system for identifying and disrupting undesirable outcomes in a patient's care, comprising:
    a non-transitory computer readable medium; and
    at least one processor programmed to perform the steps of:
        receiving patient event data provided by a patient event device, wherein the patient event data comprises physiological data generated by the patient event device;
        receiving patient action data manually input by at least one clinician associated with the patient's care, wherein the patient action data is information related to an interaction between the at least one clinician and the patient during the patient's care;
        analyzing the patient event data and the patient action data and, based on the analysis, identifying a first critical event related to the patient's care;
        comparing the patient event data and the patient action data to the first critical event;
        identifying, based on the comparison, a causal link from the patient event data and the patient action data that resulted in the first critical event;
        determining, based on the identified causal link, a first intervention to aid in disrupting a second critical event;
        wherein the first intervention provides at least one instruction to avoid the second critical event;
        determining a second intervention, distinct from the first intervention, to aid in disrupting the second critical event, based on the identified causal link; and
        determining a superior intervention based on the first intervention, the second intervention, and a determining factor.

2. The system of claim 1, wherein the patient event device includes at least one item selected from the group consisting of an interactive bed, a telemetry system, a ventilator system, an IV pump, a thermometer, a nurse call light system, an O2 saturation system, and a RTLS/RFID locating system.

3. The system of claim 2, wherein one of the first intervention, the second intervention, or the superior intervention identifies critical event data leading to the first critical event and provides instructions to avoid the second critical event in the future.

4. The system of claim 3, wherein the first critical event is determined based on predetermined criteria for recognizing undesirable outcomes.

5. The system of claim 2, wherein the action data comprises data not automatically input via the patient event device.

6. The system of claim 1, wherein the patient event data and the patient action data include corresponding location data to maintain a record of origin for the event and the action.

7. The system of claim 1, wherein one of the first intervention, the second intervention, or the superior intervention identifies the patient event data and the patient action data leading to the first critical event and provides instructions to avoid the second critical event in the future.

8. The system of claim 1, wherein the instructions provide information to prevent future patient falls.

9. The system of claim 1, wherein the instructions provide information to alter patient medication.

10. The system of claim 1, wherein the determining factor is a cost that is lower than the calculated cost of either the first intervention the second intervention, or the superior intervention.

11. The system of claim 1, wherein the determining factor is staff availability.

12. A system for identifying and disrupting undesirable outcomes in a patient's care, comprising:
    a non-transitory computer readable medium; and
    at least one processor programmed to perform the steps of:
    receiving patient event data provided by a patient event device, wherein the patient event data comprises physiological data generated by the patient event device;
    receiving patient action data manually input by at least one clinician associated with the patient's care, wherein the patient action data is information related to an interaction between the at least one clinician and the patient during the patient's care;
    analyzing the patient event data and the patient action data and, based on the analysis, identifying a first critical event related to the patient's care;
    comparing the patient event data and the patient action data to the first critical event and, based on the comparison, identifying a causal link from the patient event data and the patient action data that resulted in the first critical event;
    based on the identified causal link, determining a first intervention to aid in disrupting a second critical event;
    based on the identified causal link, determining a second intervention, distinct from the first intervention, to aid in disrupting the second critical event; and
    determining a superior intervention based on the first intervention, the second intervention, and a determining factor,
    wherein the superior intervention is determined by the at least one processor calculating a lower cost for the superior intervention than the cost of either the first intervention or the second intervention.

13. The system of claim 12, wherein the determining factor is staff availability.

14. The system of claim 12,
    wherein the determining factor is a first determining factor,
    wherein the step of determining the superior intervention is further based on a second determining factor.

15. The system of claim 14, wherein the second determining factor is a cost that is lower than the calculated cost of either the first intervention or the second intervention.

16. The system of claim 15, wherein the first intervention identifies critical event data leading to the first critical event and provides instructions to avoid the second critical event in the future.

17. The system of claim 12, wherein the patient event device includes at least one item selected from the group consisting of an interactive bed, a telemetry system, a ventilator system, an IV pump, a thermometer, a nurse call light system, an O2 saturation system, and a RTLS/RFID locating system.

18. The system of claim 17, wherein the first critical event is determined based on predetermined criteria for recognizing undesirable outcomes.

* * * * *